United States Patent
Cheng et al.

(10) Patent No.: US 11,879,859 B2
(45) Date of Patent: Jan. 23, 2024

(54) PROCESS FOR DETERMINING THE TYPE OF A DIAMOND

(71) Applicant: GOLDWAY TECHNOLOGY LIMITED, Hong Kong (CN)

(72) Inventors: Ka Wing Cheng, Hong Kong (CN); Yau Chuen Yiu, Hong Kong (CN); Kong Chan, Hong Kong (CN); Chun Hong Sham, Hong Kong (CN); Juan Cheng, Hong Kong (CN); Koon Chung Hui, Hong Kong (CN)

(73) Assignee: GOLDWAY TECHNOLOGY LIMITED, Hong Kong (CN)

( * ) Notice: Subject to any disclaimer, the term of this patent is extended or adjusted under 35 U.S.C. 154(b) by 0 days.

(21) Appl. No.: 17/633,135

(22) PCT Filed: Aug. 5, 2020

(86) PCT No.: PCT/CN2020/107148
§ 371 (c)(1),
(2) Date: Feb. 4, 2022

(87) PCT Pub. No.: WO2021/023229
PCT Pub. Date: Feb. 11, 2021

(65) Prior Publication Data
US 2022/0268718 A1 Aug. 25, 2022

(30) Foreign Application Priority Data
Aug. 5, 2019 (HK) .................... 19127777.1

(51) Int. Cl.
*G01N 24/10* (2006.01)
*G01N 33/38* (2006.01)
*G01R 33/32* (2006.01)

(52) U.S. Cl.
CPC .......... *G01N 24/10* (2013.01); *G01N 33/381* (2013.01); *G01R 33/323* (2013.01)

(58) Field of Classification Search
CPC .... G01N 24/10; G01N 33/381; G01R 33/323; G01R 33/60
See application file for complete search history.

(56) References Cited

U.S. PATENT DOCUMENTS

2007/0058775 A1    3/2007    Benderly

FOREIGN PATENT DOCUMENTS

| CN | 105738845 A | 7/2016 |
| CN | 106053513 A | 10/2016 |

(Continued)

OTHER PUBLICATIONS

International Search Report and Written Opinion of International Searching Authority for International Application No. PCT/CN2020/107148.

(Continued)

*Primary Examiner* — Jay Patidar
(74) *Attorney, Agent, or Firm* — JCIP; Joseph G. Chu; Jeremy I. Maynard (57) ABSTRACT

A process for determining the type of a diamond having spin properties and physical properties, said process including the steps of: (i) determining the spin properties of a diamond of unknown type, using optically detected magnetic resonance to measure the spin properties of said diamond of an unknown type, wherein the spin properties are indicative of the physical properties of the diamond; (ii) comparing the spin properties of said unknown diamond with the spin properties of a plurality of diamonds of known types; and (iii) determining the type of said diamond of unknown type upon a predetermined threshold of correlation between the spin properties of said diamond of unknown type with the (Continued)

spin properties of a diamond of known type of said plurality of diamonds known types.

11 Claims, 6 Drawing Sheets

(56) References Cited

FOREIGN PATENT DOCUMENTS

| | | | | |
|---|---|---|---|---|
| CN | 106414818 A | 2/2017 | | |
| CN | 107024495 A | 8/2017 | | |
| CN | 108918485 A | 11/2018 | | |
| CN | 109270478 A | 1/2019 | | |
| CN | 109709128 A | 5/2019 | | |
| GB | 2275788 A | * 9/1994 | ............ | G01N 21/87 |
| JP | 03239978 A | 10/1991 | | |
| RU | 2570471 C1 | 7/2000 | | |
| RU | 2569791 C1 | 11/2015 | | |
| TW | 528422 U | 9/2016 | | |
| WO | 02068946 A1 | 9/2002 | | |

OTHER PUBLICATIONS

Dmitriev A.K. et al. "Multi-frequency ODMR of Nitrogen-Vacancy Color Centers in Diamond Crystals in zero magnetic fields" Journal of Physics: Conference Series, vol. 1135, No. 1, Dec. 31, 2018 (Dec. 31, 2018), pp. 1-10.
Hong Kong Search Report for Application No. 19127777.1.

* cited by examiner

PROCESS FOR DETERMINING THE TYPE OF A DIAMOND

TECHNICAL FIELD

The present invention relates to a process and system for determining properties of a diamond. particularly, the present invention provides a process and a for authentication and determining the type of a diamond.

BACKGROUND OF THE INVENTION

As is known, diamonds are typically considered to be luxury item and are often utilized in luxury goods, such as items of jewellery, and are known to often be of a very high value. As such, diamond authentication has become increasingly important with the rise of new technologies in respect of synthetic diamonds and the manufacture thereof.

A natural diamond is typically considered a rare item, and natural diamonds have been reported as having been formed between millions and 3.5 billion years ago, and being formed with the earth, and have been reported as being formed at depths between 150 and 250 kilometers below the surface of the earth.

As is known, the clarity, cut, carat and colour of a diamond influence the value of a diamond. Diamonds of higher value are typically those of very little or no discernable colour, which is typically a subtle yellow tinge, and of higher clarity, that is with fewer visible defects or inclusions with the body of the diamond.

In more recent years, synthetic or non-natural diamonds have been produced, which are formed or grown in a laboratory, and man-made, which are made in a controlled laboratory environment that purported to reflect the conditions needed for diamonds to form in nature. There are two processes to create man-made diamonds; chemical vapor deposition (CVD diamonds) and high pressure high treatment (HPHT diamonds).

A CVD (chemical vapor deposition) diamond is a laboratory made diamond, which is created through the process of chemical vapor deposition. This method is often used for larger stones.

An HPHT (high pressure high temperature) diamond is a laboratory made diamond used with a process called high pressure high treatment. HPHT is primarily used for small diamond melee, not usually for larger stones.

Laboratory made diamonds are considered to be real diamonds, and are comprised of mineral consisting of pure carbon crystallized in the isometric system, and the differences are indistinguishable to the naked eye and nearly if not impossible under magnification.

Such synthetically formed diamonds are considered to be "real", and grading authorities may issue one report for natural diamonds and a separate report for laboratory made diamonds. Both reports provide a full 4Cs assessment for cut, clarity, color, and carat. All diamonds undergo the same rigorous grading process.

Non-natural (i.e. laboratory made) diamonds are generally of a lower economic value, and can be considered non-authentic or at least non-traditional.

As part of the value of a natural diamond, the age, millions or billions of years, and the scarcity and unique nature between every diamond, drives the value of such diamonds. Further, the history of a diamond also may contribute to its value, and at least sentimental value when a diamond has been gifted or passed down through generations in a family.

Not surprisingly, the advent of high quality synthetically formed diamonds, such as CVP and HPHT diamonds, has had a significant effect in the diamond industry.

There have been instances of natural diamonds being replaced with synthetic diamonds, as part of fraudulent activities, with the real owner not being aware of such deceit.

There have been numerous instances of high-quality synthetic diamonds being passed off to customers as being real diamonds, or real diamonds having full documentation being substituted by synthetic diamonds between purchase and collection.

Traditionally, optical methods, such as Fourier transform infrared (FTIR) and Raman spectroscopies have been utilised to seek to distinguish natural diamonds from synthetic diamonds effectively.

However, due to the great advance in CVD and HPHT technologies for synthetic diamonds in recent years, making discernment increasingly difficult between the different types.

Furthermore, some low grade natural diamonds can even be treated with HPHT to become high grade diamonds, thus modifying the value of a diamond whilst representing the diamond to be naturally occurring at that grade.

Therefore, diamond authentication so as to determine the type of diamonds, that is natural and unmodified diamonds, versus synthetic or modified natural diamonds, has become increasingly difficult, and existing processes for determining diamond type are increasingly less reliable and uncertain and inevitably shall become obsolete in the near future. Therefore, new methodologies to identify natural, synthetic and treated diamonds are needed.

OBJECT OF THE INVENTION

It is an object of the present invention to provide a process and a system for authentication of a diamond and type of diamond, which overcomes or at least partly ameliorates at least some deficiencies as associated with the prior art.

SUMMARY OF THE INVENTION

In a first aspect, the present invention provides a process for determining the type of a diamond, said process including the steps of:
  (i) determining the spin properties of a diamond of unknown type, using optically detected magnetic resonance to measure the spin properties of said diamond of an unknown type, wherein the spin reflect the physical properties of the diamond;
  (ii) comparing the spin properties of said unknown diamond with the spin properties of a plurality of diamonds known types; and
  (iii) determining the type of said diamond of unknown type upon a predetermined threshold of correlation between the spin properties of said diamond of unknown type with the spin properties of a diamond of known type of said plurality of diamonds known types.

The spin properties include resonance frequency, broadening, and spin lifetime.

The physical properties include inclusions, defects, crystallinity inconsistency, deformation of crystal lattice, internal stress, internal stress, impurities and uniformity.

The process may include the use of a fluorescence microscope.

The types of diamond include natural diamonds, chemical vapor deposition (CVD) synthetic diamonds, high pressure high temperature (HPHT) synthetic diamonds, and treated natural diamonds.

The diamond may be a synthetic diamond, such as a CVD or HPHT diamond, or combination thereof.

The diamond may be a treated diamond, treated by HPHT or CVD or combination thereof.

In a second aspect, the present invention provides a system for determining the type of a diamond, said system comprising:
- a magnetic field generator for applying a magnetic field to a diamond of unknown type;
- a microwave frequency generator for applying a variable microwave frequency to said diamond;
- an excitement laser module for applying a laser input signal to said diamond, wherein said excitement laser module excites NV– centres or other C centres within the diamond; and
- a fluorescence detector for detecting and acquiring the intensity of fluorescence from said NV⁻ centres or other C centres of the diamond throughout the frequency range of the microwave generator, The system may further comprise a processor module for receiving light intensity from the fluorescence detector and microwave frequency data, and an output module for providing an output signal indicative of the diamond type of said diamond, wherein upon a predetermined threshold of correlation between light intensity versus microwave frequency characteristics of said diamond of unknown type with light intensity versus microwave frequency characteristics diamond of known of a plurality of diamonds known types, said output module provides a signal indicative the type of said diamond.

The types of diamond may be natural diamonds chemical vapor deposition (CVD) synthetic diamonds, high pressure high temperature (HPHT) synthetic diamonds, and treated natural diamonds.

The fluorescence detector may be a fluorescence microscope and further includes objective lenses, and may include a focusing stabilizer.

The fluorescence microscope may be operated in sample scanning mode or laser scanning mode.

The excitation laser module may be composed of continuous wave green laser of wavelength for example 514 nm or 532 nm equipped with linear polarizer and half wave plate for controlling laser power.

The system may further comprise a sample stage which is composed of an XYZ 3-axis electrically motorized mechanical stage and a XYZ 3-axis piezo stage for achieving sample scanning.

The system may further comprise a sample holder with said microwave frequency generator supplier is a holder for binding a cut diamond with a microwave emitter.

The system may comprise are two objective lenses which are dry air immersed objective lens and oil immersed objective lens for illuminating laser onto diamond and collection of the resultant fluorescence.

The focusing stabilizer is preferably for fine control of objective lenses distance between objective lens and oil immersed objective lens.

In a third aspect, the present invention provides a process of determining the type of a diamond of unknown type, said process including the steps of:
(i) applying a laser input signal to a diamond of unknown type with the NV⁻ centres or other C centres such that fluorescence is generated from said diamond;
(ii) applying a magnetic field to said diamond and applying a variable microwave frequency to said diamond;
(iii) acquiring the light intensity of fluorescence as a function of microwave frequency; and
(iv) determining the type of the unknown diamond by comparing the light intensity of fluorescence as a function of microwave frequency of (iii) with light intensity versus microwave frequency characteristics diamond of known of a plurality of diamonds known types.

The types of diamond may be natural diamonds chemical vapor deposition (CVD) synthetic diamonds, high pressure high temperature (HPHT) synthetic diamonds, and treated natural diamonds.

In a fourth aspect, the present invention provides a process operable using a computerized system for determining the type of a diamond, wherein the spin properties of a diamond of unknown type are correlated with the spin properties of a plurality of diamonds each of known type, the computerized system including a system for determined the spin properties of a diamond, a processor module and an output module operably interconnected together, said process including the steps of:
(i) acquiring via a system for determined the spin properties of a diamond, data indicative of the spin properties of a diamond of unknown type;
(ii) in a processor module, comparing said data indicative of the spin properties of the diamond of unknown type image with a plurality of data sets each of which corresponds to the spin properties of a plurality diamonds each of known type; and'
(iii) from an output module, responsive to a predetermined threshold of correlation between the data derived from step (i) and one of the plurality of data sets from step (ii), an output signal is provided indicative of the type of the diamond.

In a fifth aspect, the present invention provide a process operable using a computerized system for determining the type of a diamond using a pre-trained neural network for determination of a diamond type, the computerized system including a system for determining the spin properties of a diamond, a pre-trained neural network and an output module operably interconnected together via a communication link, said process including the steps of:
(i) acquiring via the system for determining the spin properties of a diamond data indicative of the spin properties of a diamond of unknown type;
(ii) in a pre-trained neural network, determining the type of diamond of said diamond of unknown type from the data indicative of the spin properties of the diamond of unknown type acquired in step (i)
  wherein the pre-trained neural network has been pre-trained utilising a plurality of data sets each of which corresponds to spin properties of a plurality diamonds each of known type; and
(iii) from an output module, providing the type of said diamond.

In a sixth aspect, the present invention provides a computerized system for determining the type of a diamond wherein the spin properties of a diamond of unknown type is correlated with spin properties of a plurality of diamonds each of known type, the computerized system including:
- a system, for determining the spin properties of a diamond for acquiring data indicative of the spin properties of a diamond of unknown type
- a processor module for comparing said data indicative of the spin properties of the diamond of unknown type with a plurality of data sets each of which corresponds to the spin properties of a plurality diamonds each of known type; and an output module for providing an output signal indicative of the type of said diamond of unknown type, upon a predetermined threshold of correlation between said data indicative of the spin properties of a diamond of unknown type and one of the plurality of data sets which corresponds to the spin properties of a plurality diamonds each of known type.

The system for determining the spin properties of a diamond may include:

a magnetic field generator for applying a magnetic field to a diamond of unknown type;

a microwave frequency generator for applying a variable microwave frequency to said diamond;

an excitement laser module for applying a laser input signal to said diamond, wherein said excitement laser module excites $NV^-$ centres or other C centres within the diamond; and a fluorescence detector for detecting and acquiring the intensity of fluorescence from said $NV^-$ centres or other C centres of the diamond throughout the frequency range of the microwave generator.

BRIEF DESCRIPTION OF THE DRAWINGS

In order that a more precise understanding of the above-recited invention can be obtained, a more particular description of the invention briefly described above will be rendered by reference to specific embodiments thereof that are illustrated in the appended drawings. The drawings presented herein may not be drawn to scale and any reference to dimensions in the drawings or the following description is specific to the embodiments disclosed.

DETAILED DESCRIPTION OF THE DRAWINGS

The present inventors have identified shortcomings in the manner in the prior art, and upon identification of the problems with the prior art, have provided a system and process which overcomes the problems of the prior art.

For the purposes of this invention, the term "type" of diamond is defined as and is understood to be natural diamonds, chemical vapor deposition (CVD) synthetic diamonds, high pressure high temperature (HPHT) synthetic diamonds, and treated natural diamonds, all of which are different types of diamonds.

1. Background of Invention

In order to identify whether a diamond is natural or not such as a CVD or a HPHT diamond, or is a natural diamond which may have been treated to have its properties altered, the physics inside the material can be utilized to make such a determination as to the type of diamond.

Diamond contains impurities, and by understanding the physical properties of the impurities in accordance with the present invention the manner in which the diamond is formed may be formed, and such phenomena and the determination and use thereof, has been provided by the present invention in order to ascertain the type of a diamond.

Accordingly, the present invention provides a process and a system determining the type of a diamond.

The type of diamond, such as natural diamond, chemical vapor deposition (CVD) synthetic diamonds, high pressure high temperature (HPHT) synthetic diamonds, and treated natural diamonds can be determined.

In particular, the present invention is useful in determining whether a diamond is a naturally occurring diamond, or whether the diamond is a synthetic diamond, or a treated diamond The type of diamond is determined by:

(i) determining the spin properties of a diamond of unknown type, using optically detected magnetic resonance to measure the spin properties of said diamond of an unknown type, wherein the spin reflect the physical properties of the diamond;

(ii) comparing the spin properties of said unknown diamond with the spin properties of a plurality of diamonds known types; and (iii) determining the type of said diamond of unknown type upon a predetermined threshold of correlation between the spin properties of said diamond of unknown type with the spin properties of a diamond of known type of said plurality of diamonds known types.

Such threshold may be determined by mathematical analysis, or by a processor, or an automatic computer operable process.

Alternatively, a pre-trained artificial intelligence system may be used, utilising pre-trained neural network.

Figure 1A:
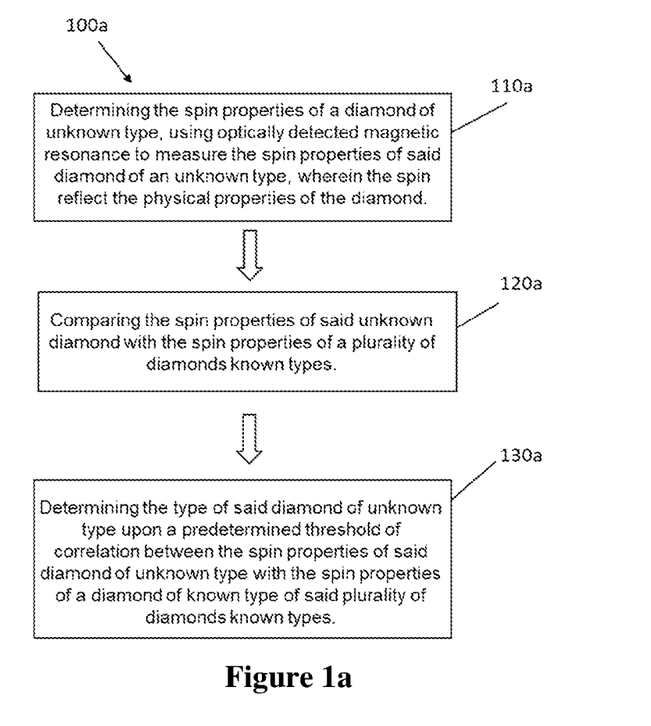
FIG. 1a shows a schematic representation of an example of the process of the present invention.

Referring to FIG. 1a, there is a flow chart of the process 100a according to the present invention. As will be understood, the process can be implemented in a computerized system, and further in embodiments the process may utilise a pre-trained neural network.

In the process 100a, the following steps apply for determining the type of diamond is determined by:

Step 1 (110a)—determining the spin properties of a diamond of unknown type, using optically detected magnetic resonance to measure the spin properties of said diamond of an unknown type, wherein the spin reflect the physical properties of the diamond;

Step 2 (120b)—comparing the spin properties of said unknown diamond with the spin properties of a plurality of diamonds known types; and Step 3 (130c) determining the type of said diamond of unknown type upon a predetermined threshold of correlation between the spin properties of said diamond of unknown type with the spin properties of a diamond of known type of said plurality of diamonds known types.

Figure 1B:
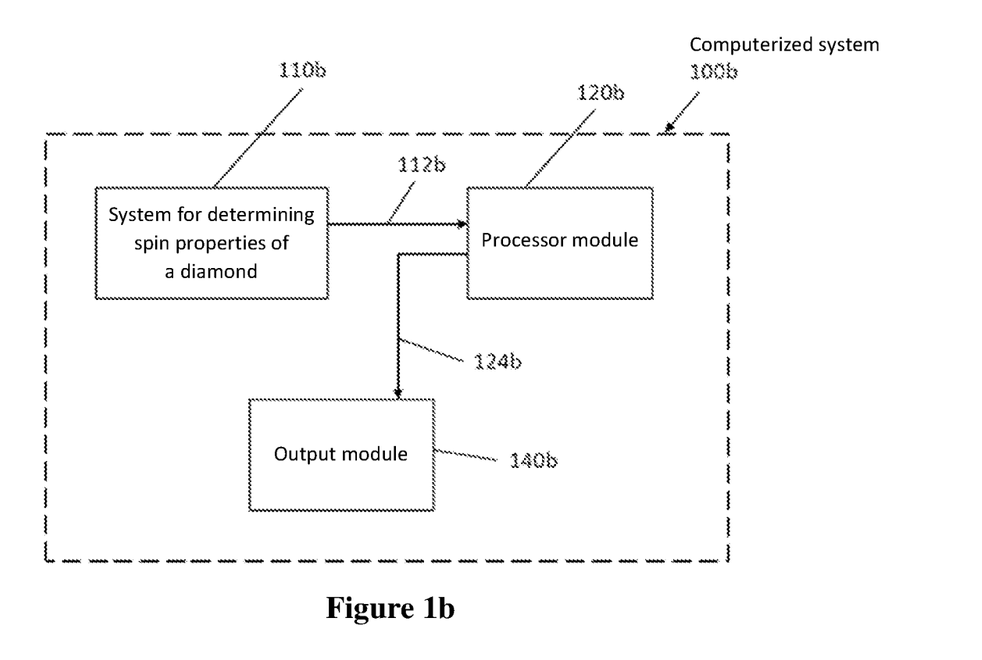
FIG. 1b shows a schematic representation of an example a system of the present invention.

Referring to FIG. 1b, there is shown an example of a computerized system 100b according to the present invention for determining the type of a diamond wherein the spin properties of a diamond of unknown type is correlated with spin properties of a plurality of diamonds each of known type.

The computerized system 100b includes a system for determining the spin properties of a diamond 110b for acquiring data indicative of the spin properties of a diamond of unknown type The computerized system 100b further includes a processor module 120b in communication 112b with system for determining the spin properties of a diamond 110b, for comparing said data indicative of the spin properties of the diamond of unknown type with a plurality of data sets each of which corresponds to the spin properties of a plurality diamonds each of known type.

The computerized system 100b further includes an output module 140b in communication with processor module 120b, for providing an output signal indicative of the type of said diamond of unknown type, upon a predetermined threshold of correlation between said data indicative of the spin properties of a diamond of unknown type and one of the plurality of data sets which corresponds to the spin properties of a plurality diamonds each of known type.

2. Nitrogen-Vacancy (NV) Centres of Diamonds

Diamond colour centre has gained attention in quantum technologies, especially for nitrogen-vacancy (NV) centres.

Diamond NV centre is a carbon atom in the tetrahedral structure replaced by a nitrogen atom and another carbon next to the replaced atom missing.

NV centres emit fluorescence under light excitation in suitable wavelength range.

The NV centre can capture an electron from its surrounds in order to gain a negative charge to become a NV⁻ centre.

Diamond NV⁻ centre exhibits a total spin of 1, and has been considered to provide applications of quantum sensing. By utilising the spin properties of diamond NV⁻ centre, it is possible to detect very subtle difference in physical properties of a diamond.

3. Optically Detected Magnetic Resonance (ODMR) and Present Invention

Optically detected magnetic resonance (ODMR) is a method to manipulate the spin in diamond NV⁻ centre, the incorporation into the present invention which has been considered by the present inventors useful in achieving the objectives of the present invention.

ODMR can be considered an optical version of electron paramagnetic resonance (EPR) to detect the change of either emitted or absorbed light associated with the paramagnetic centre, when the population redistribute among magnetic sublevels with magnetic resonance in the ground or excited state of the paramagnetic centre.

Since the magnetic sublevels can be split by magnetic field, which is known as the Zeeman effect, the sublevels are separated by very small amount of energy in the microwave region.

In the case of resonance of a microwave frequency with the sublevel energy, the magnetic field splits the sublevels matching microwave frequency such that the emission or absorption of light is changed or altered.

The present inventors have noted that the spin of the NV centre is extremely sensitive to the environment within a diamond, such as the presence of impurities, internal strain, internal stress, inconsistencies in the crystal lattice of a diamond, and have thus in view of such observations, proposed the process and system of the present invention to sense the physical conditions in a diamond and thus identify its formation method, and thus determined the "type" of diamond under assessment or evaluation.

4. NV⁻ Centre and Present Invention

Optically detected magnetic resonance ODMR can be achieved with samples containing unpaired electrons or non-vanished total electron spins. This technique utilizes the optical method to realize the electron spin states transition under influence by external microwave and internal or external magnetic field respect to the sample.

Figure 1C:
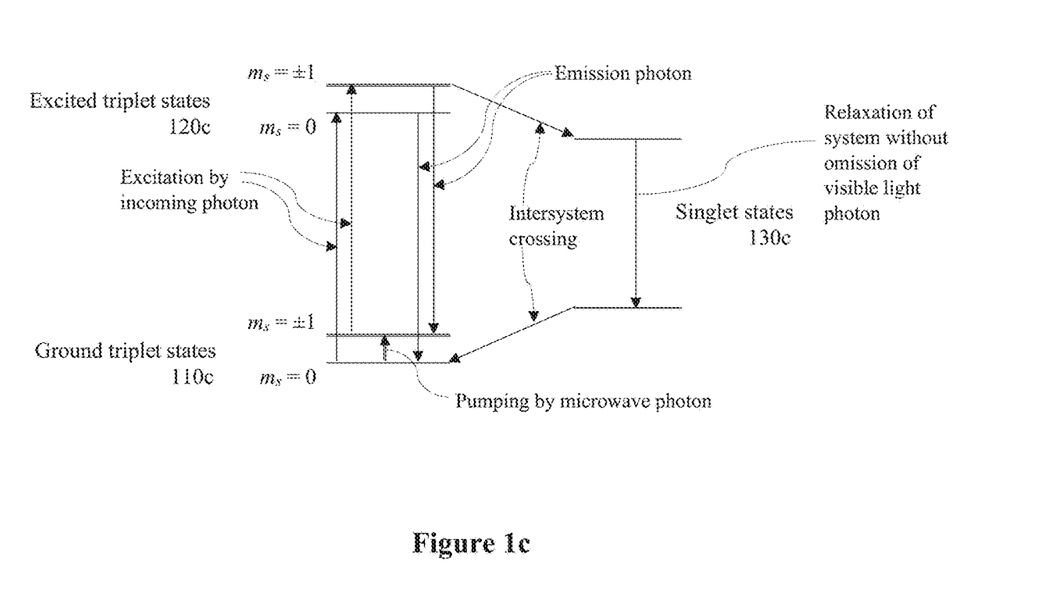
FIG. 1c is a schematic representation of the energy level of a diamond $NV^-$ centre, and as utilized in accordance with the present invention.

Referring to FIG. 1c, for a diamond NV⁻ centre, its electronic structure contains a triplet ground state 110c and a triplet excited state 120c, which have $m_s=0$ and $m_s=\pm 1$.

Companion with the system, there are also two singlet states 130c.

Normally, when a 532 nm photon interacts with the system with $m_s=0$, the system subsequently returns to the ground states 110 by emitting a 637 nm photon.

Alternatively, if the 532 nm photon interacts with the system with $m_s=\pm 1$, it may be possible that a 637 nm photon can still be emitted when the system returns to the ground states 110. However, there may also be chances that the system may relax through intersystem crossing via the singlet states 130 and finally return to the $m_s=0$ ground state 110. Since this path will not emit photon in visible range, the light generated by this pathway is weaker.

Therefore, when a microwave photon interacts with the system, the system changes from the $m_s=0$ ground state to $m_s=\pm 1$ ground state. This will generate a weaker light.

The presence of internal or external magnetic fields may create electron spin states splitting in the order of microwave energy scale. The splitting can be shown by the fluorescence from the sample. Light energy can excite the sample from ground electronic and spin states to excited electronic and spin states. The sample will then decay back to ground state by releasing energy in form of light or heat.

During the excitation and decay processes, the electron spin states of the sample could be switched between fluorescence-active and fluorescence-inactive electron spin states. Microwave will be absorbed by the sample when there is any allowed transition between any two fluorescence-active and fluorescence-inactive electron spin states. And thus, fluorescence from the sample will be suppressed.

By scanning the influenced microwave frequency, one can expect an observable stable fluorescence from the sample and then a sudden dimmed fluorescence when the microwave frequency matches with transition from fluorescence-active electron spin states to fluorescence-inactive electron spin states.

Figure 2:
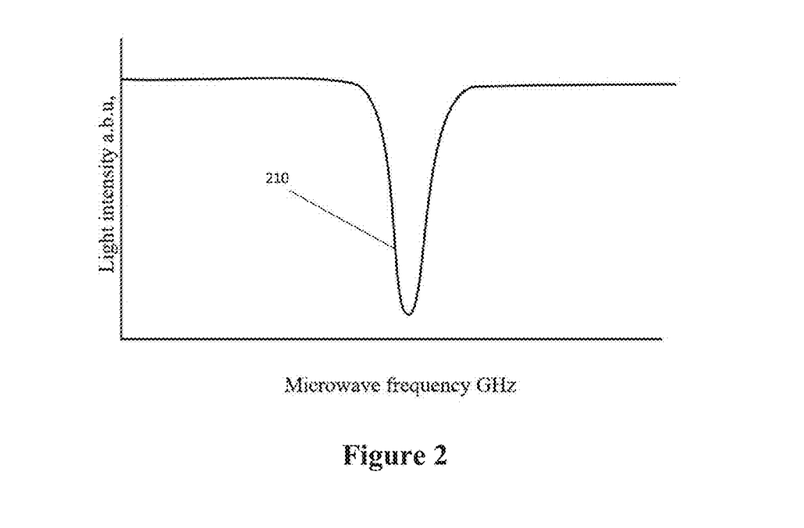
FIG. 2 shows a light intensity drop at resonance as a dip in ODMR without external magnetic field.

Referring to FIG. 2, as is shown by sweeping the microwave frequency without magnetic field, it will show a dip 210 in optical intensity (which is measured in the unit of normalized arbitrary unit) at around 2.87 GHz.

As discussed, such a dip 210 in the light intensity is due to the resonance condition in which the input microwave frequency (2.87 GHz) matches with that required for the transition of the system from ground state $m_s=0$ to $m_s=+1/-1$. As the fluorescence-active electron spin state is transited to the fluorescence-inactive electron spin states, fluorescence from NV centers of diamond would be suppressed and thus, a fluorescence dip 210 would be obtained. Now referring to FIG. 3 as shown, in the presence of magnetic field, the $m_s=\pm 1$ states are split by Zeeman effect.

Figure 3:
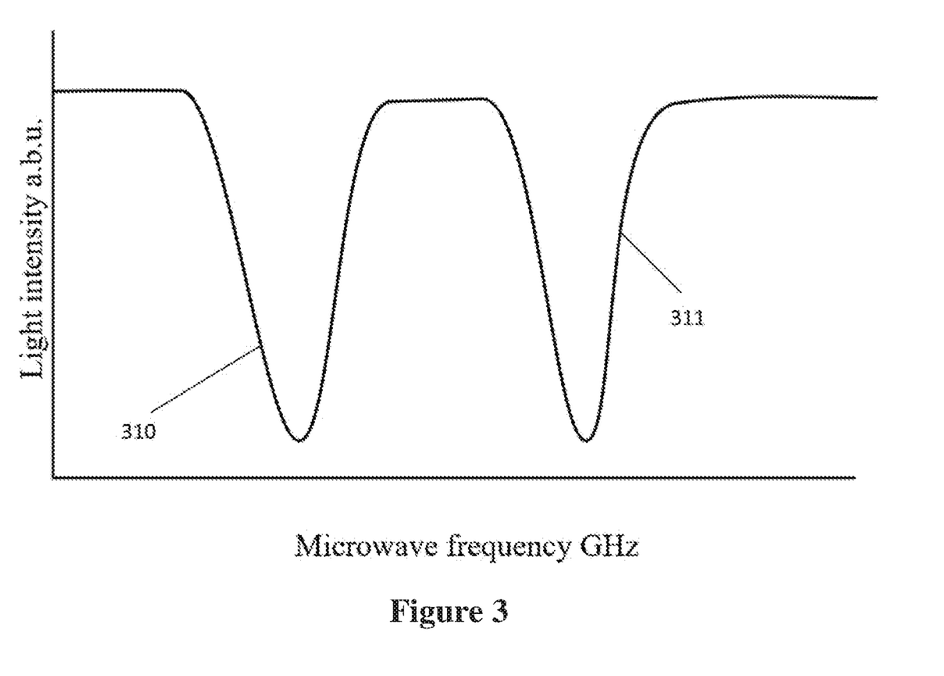
FIG. 3 shows a light intensity drop at resonance as double dips in ODMR with external magnetic field.

Therefore, instead of a single dip in the optical intensity, the optical intensity shows two dips 310, 311 with the width in between the dips being proportional to the magnetic field strength.

The applied magnetic field cause Zeeman effect, which splits the degenerated states $m_s=+1/-1$ in to two separated states. The energy state which is parallelly aligned with respect to the applied magnetic field direction is the lower energy state, while the energy state which is anti-parallelly aligned with respect to the applied magnetic field direction is the higher energy state.

Therefore, upon the presence of a magnetic field, there exists two available transitions instead of the only one. By repeating experiment describe in FIG. 2, one can observe two dips 310, 311 which are located at the left and right side to the original dip 210 of FIG. 2.

For a natural diamond, since its formation process was in a scale of millions of years or longer, it normally has a lower internal strain.

For a synthetic diamond, depends on its formation method, it can have larger (normally in CVD), or a lower strain than for a natural diamond.

Moreover, since a synthetic diamond has a shorter formation time than natural diamond, a synthetic diamond typically shows more homogenous physical properties than a natural diamond.

The present inventors have found that all these characteristics can be detected by use of ODMR.

For difference in strain, the microwave resonance frequency or dip positions in ODMR can be different.

Moreover, since the spin lifetime is affected by strain within a diamond, a natural diamond normally has a longer spin lifetime because of the lower strain.

By analyzing the statistics and characteristics of dip positions and spin lifetimes of diamonds, a diamond can be authenticated and its type thus determined.

Figure 4A:
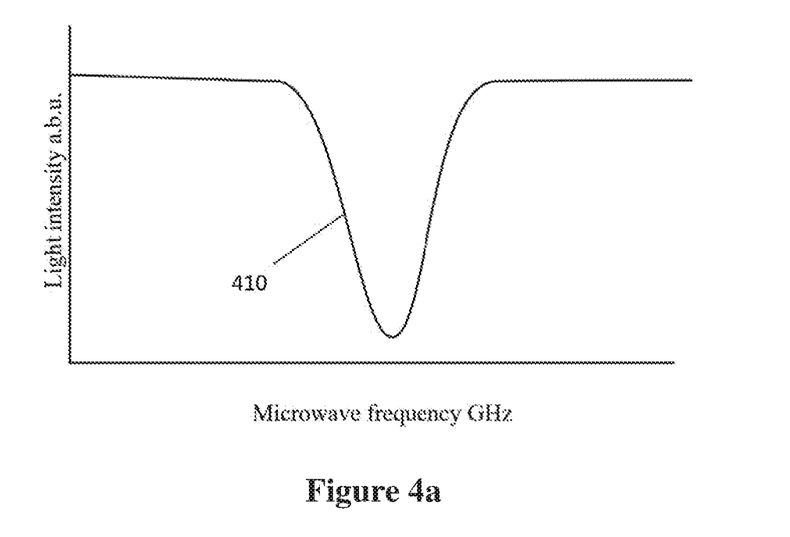
FIG. 4a shows a natural diamond has a boarder dip for light intensity versus microwave frequency.

FIG. 4a shows the ODMR result of a natural diamond where a dip 410 is observed. Such a dip 410 has a broad resonance width of microwave frequency.

Figure 4B:
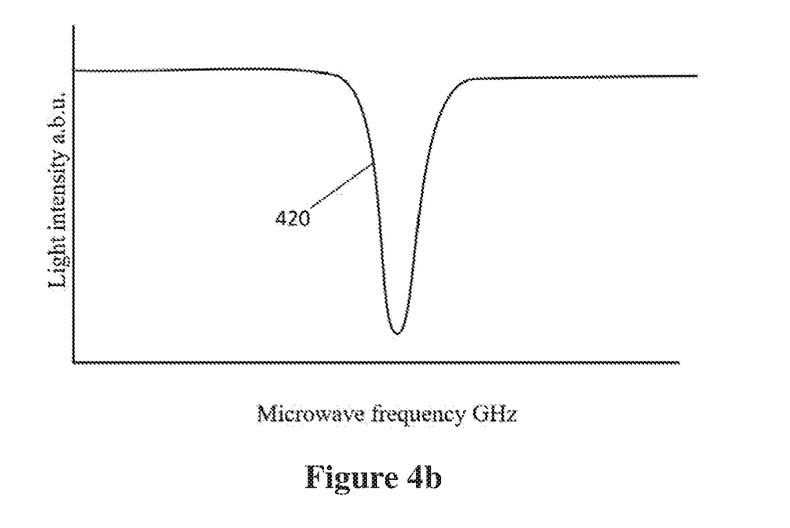
FIG. 4b shown a synthetic diamond having a narrower dip for light intensity versus microwave frequency.

This is in contrast to FIG. 4b which shows the ODMR result of a synthetic diamond. It can be observed that the width of the dip 420 is of a much narrower width to the dip 410 of a natural diamond. This may be due to the fact that synthetic diamonds, since it have a shorter formation time, have more homogenous physical properties and evenly distributed NV center interaction.

Therefore, in accordance with the present invention, synthetic diamonds can be screened out by their narrower dip width.

5. Examples of Present Invention

Figure 5:
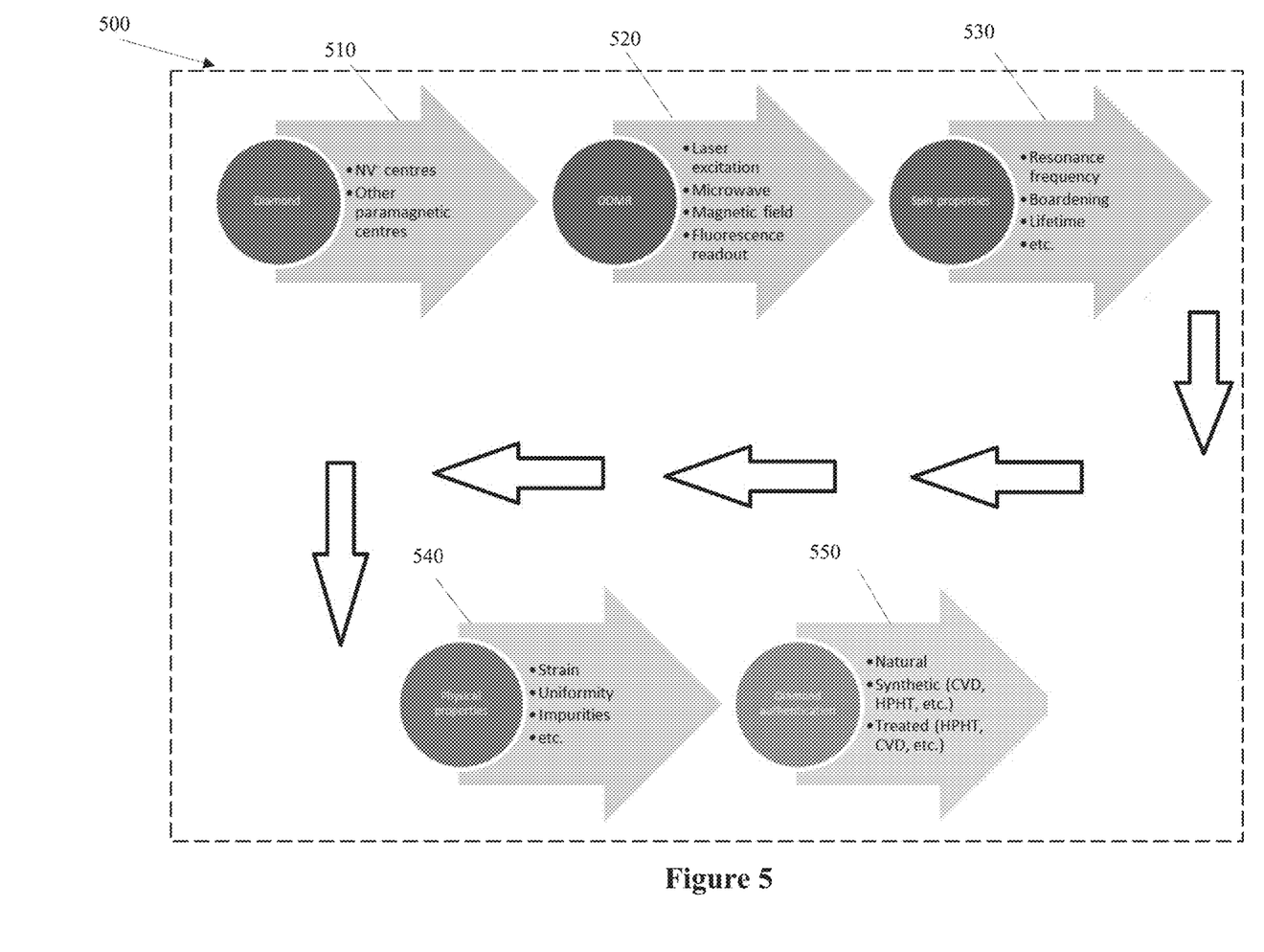
FIG. 5 shows a flow chart of an embodiment of the process according to the present invention.

Referring to FIG. 5, there is shown a flow chart of the process 500 for determining the type of a diamond.

In accordance with the invention, spin properties of a diamond 510 are used for determining the type of diamond. $NV^-$ or other paramagnetic c centres.

A diamond of unknown type is excited 520, typically by a laser of a predetermined and appropriate wavelength. A magnetic field is applied to the diamond, and a microwave signal, typically in the GHz band, is applied, and whereby the frequency can be varying across an appropriate frequency range.

The excited diamond causes fluorescence from the laser, and upon application of the microwave energy, the dip in light intensity characteristic as described above is achieved due to resonance 530, and the characteristics of intensity of the fluorescence is detected by a fluorescence detector such as a fluorescence microscope.

The spin properties of the NV centres or other paramagnetic c centres are influenced by the physical properties 540 of the diamond, such as inclusions, defects, crystallinity inconsistency, deformation of crystal lattice, internal stress, internal stress, impurities and uniformity.

Those physical properties vary between types of diamonds, such as natural diamonds, synthetic CVD or HPHT diamonds, treated natural diamonds, treated CVD or HPHT diamonds.

Thus, the spin properties and hence the light intensity versus microwave frequency response curves have characteristics indicative of the type of diamond, thus allowing for assessment of the type of diamond 550 in accordance with the present invention.

Figure 6:
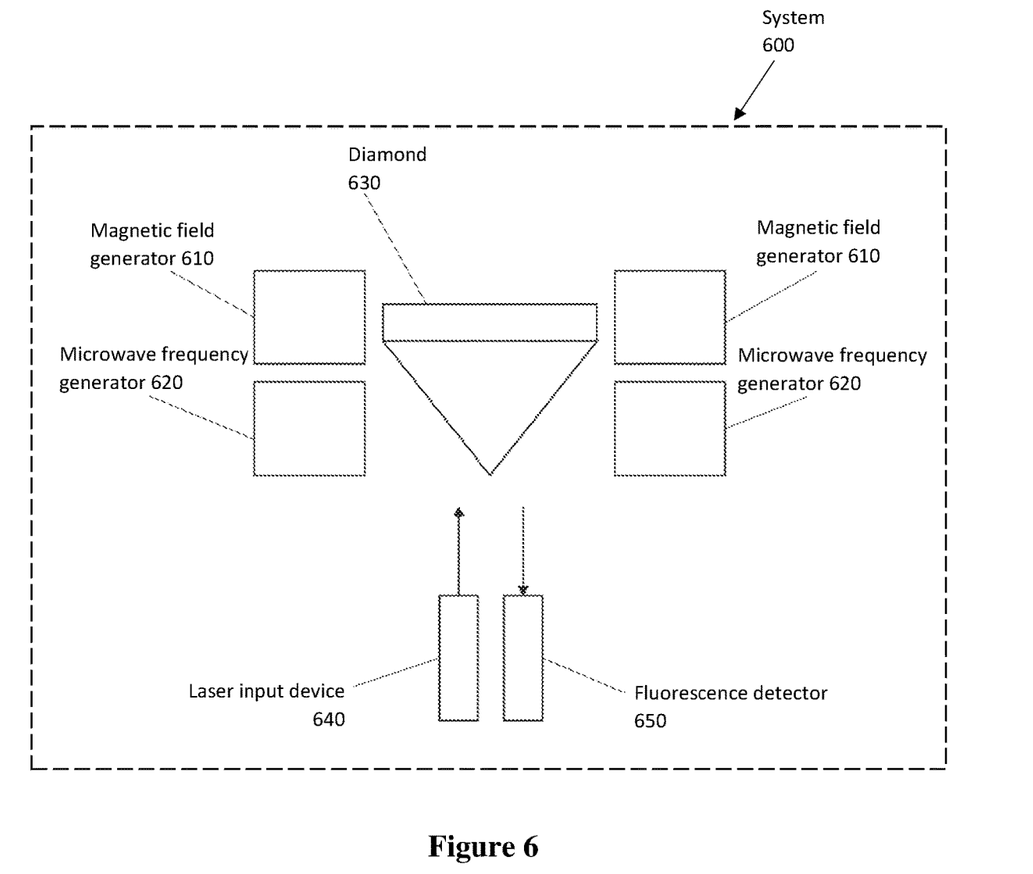
FIG. 6 shows an embodiment of the system according to the present invention.

Referring to FIG. 6, there is shown an embodiment of a system 600 according to the present invention, for use in determining the type of an unknown diamond embodying the process of the present invention as described above.

The system 600 include a magnetic field generator and a microwave field generative 620 for applying suitable magnetic field and variable microwave signal output in accordance with the present invention to a diamond 630 of unknown type.

A laser input device 640 provides laser light of a predetermined and suitable wavelength to excite $NV^-$ centres or other paramagnetic C centres in the diamond 630.

Such excited $NV^-$ centres or other paramagnetic C centres provide fluorescence which is detectable by a fluorescence detector 650, such as a fluorescence microscope, which allows the fluorescence light intensity to be measured as a function of the frequency of the microwave generator.

Such a response characteristic can then be compared with response characteristics of difference types of diamonds as described above and in accordance with the process as described with reference to FIG. 5, do as to determine the diamond type of the diamond 630.

This is achieved by analysis of the spin properties, whereby it has been found by the present inventors that the spin properties of a natural diamond are different to that of a synthetically formed diamond and as such, the present invention provides a non-invasive assessment process whereby based on spin properties of a diamond which can be used to determine whether a diamond is a naturally occurring diamond, or whether such a diamond may in fact be synthetically formed in a laboratory such as a CVD diamond.

Synthetic diamonds has provided under current manufacturing conditions, can be very difficult to discern from a natural diamond due to enhanced and in Increased manufacturing technologies and as such, the optical properties of such a synthetic diamond often cannot be ascertained as being different from those from a naturally occurring diamond.

Accordingly, the present invention provides a process by which natural diamonds and synthetic diamonds maybe determined as being different from each other, which is useful for various reasons, including impropriety, theft, replacement of diamonds, synthetic diamonds being passed off as being natural diamonds, and valuation of diamonds in order to determine whether a diamond is indeed naturally formed or synthetically formed.

As will be appreciated, he process according to the present invention may be implemented in various forms and embodiments and systems which embody the process, whilst utilizing the present invention In order to determine florescence lifetime so as to distinguish whether a diamond is a naturally occurring diamond or a synthetically laboratory or industry grown diamond.

The invention claimed is:

1. A process for determining a type of a diamond having spin properties and physical properties, said process including the steps of:
   (i) determining the spin properties of a diamond of unknown type, using optically detected magnetic resonance to measure the spin properties of said diamond of an unknown type, wherein the spin properties are indicative of the physical properties of the diamond;
   (ii) comparing the spin properties of said unknown diamond with the spin properties of a plurality of diamonds of known types; and
   (iii) determining the type of said diamond of unknown type upon a predetermined threshold of correlation between the spin properties of said diamond of unknown type with the spin properties of a diamond of known type of said plurality of diamonds known types.

2. The process according to claim 1, wherein the spin properties include resonance frequency, broadening, spin lifetime or combinations thereof.

3. The process according to claim 1, wherein the physical properties include inclusions, defects, crystallinity inconsistency, deformation of crystal lattice, internal stress, internal stress, impurities and uniformity.

4. The process according to claim 1, wherein the types of diamond are natural diamonds, chemical vapor deposition (CVD) synthetic diamonds, high pressure high temperature (HPHT) synthetic diamonds, and treated natural diamonds.

5. The process according to claim 1, wherein the diamond is a synthetic diamond.

6. The process according to claim 5, wherein the diamond is a CVD or HPHT diamond, or combination thereof.

7. The process according to claim 1, wherein the diamond is a treated diamond, treated by HPHT or CVD or combination thereof.

8. A process using a computerized system for determining a type of a diamond of unknown type and having spin properties, wherein the spin properties of the diamond of unknown type are correlated with the spin properties of a plurality of diamonds each of known type, the computerized system including a system for determining the spin properties of the diamond, a processor module and an output module interconnected together, said process including the steps of:
   (i) acquiring via the system for determining the spin properties of the diamond, data indicative of the spin properties of the diamond of unknown type;
   (ii) in a processor module, comparing said data indicative of the spin properties of the diamond of unknown type with a plurality of data sets each of which corresponds to the spin properties of the plurality diamonds each of known type; and'
   (iii) from an output module, responsive to a predetermined threshold of correlation between the data derived from step (i) and one of the plurality of data sets from step (ii), an output signal is provided indicative of the type of the diamond.

9. A process using a computerized system for determining a type of a diamond having spin properties using a pre-trained neural network for determination of the diamond type, the computerized system including a system for determining the spin properties of the diamond, a pre-trained neural network and an output module interconnected together via a communication link, said process including the steps of:
   (i) acquiring via the system for determining the spin properties of the diamond, data indicative of the spin properties of the diamond of unknown type;
   (ii) in a pre-trained neural network, determining the type of diamond of said diamond of unknown type from the data indicative of the spin properties of the diamond of unknown type acquired in step (i)
      wherein the pre-trained neural network has been pre-trained utilising a plurality of data sets each of which corresponds to spin properties of a plurality diamonds each of known type; and
   (iii) from an output module, providing the type of said diamond.

10. A computerized system for determining a type of a diamond of unknown type having spin properties, wherein the spin properties of the diamond of unknown type are correlated with spin properties of a plurality of diamonds each of known type, the computerized system including:
   a system for determining the spin properties of the diamond for acquiring data indicative of the spin properties of the diamond of unknown type,
   a processor module for comparing said data indicative of the spin properties of the diamond of unknown type with a plurality of data sets each of which corresponds to the spin properties of a plurality diamonds each of known type; and
   an output module for providing an output signal indicative of the type of said diamond of unknown type, upon a predetermined threshold of correlation between said data indicative of the spin properties of the diamond of unknown type and one of the plurality of data sets which corresponds to the spin properties of the plurality diamonds each of known type.

11. A system according to claim 10, wherein the system for determining the spin properties of the diamond wherein said diamond has $NV^-$ centres or other C centres and wherein said system includes:
   a magnetic field generator for applying a magnetic field to the diamond of unknown type;
   a microwave frequency generator for applying a variable microwave frequency to said diamond;
   an excitement laser module for applying a laser input signal to said diamond, wherein said excitement laser module excites said $NV^-$ centres or other C centres within the diamond such that fluorescence is generated from said diamond having an intensity; and
   a fluorescence detector for detecting and acquiring the intensity of fluorescence from said $NV^-$ centres or other C centres of the diamond throughout the frequency range of the microwave generator.

* * * * *